US00PP26404P3

(12) United States Plant Patent
Bacon

(10) Patent No.: US PP26,404 P3
(45) Date of Patent: Feb. 9, 2016

(54) NECTARINE TREE NAMED SUNECTWENTYTHREE

(50) Latin Name: ***Prunus persica* var.** *nucipersica*
Varietal Denomination: SUNECTWENTYTHREE

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 146 days.

(21) Appl. No.: 13/998,404

(22) Filed: Oct. 29, 2013

(65) Prior Publication Data

US 2015/0121578 P1 Apr. 30, 2015

(51) Int. Cl.
*A01H 5/08* (2006.01)

(52) U.S. Cl.
USPC ..... Plt./190

(58) Field of Classification Search
USPC ..... Plt./190
See application file for complete search history.

*Primary Examiner* — Anne Grunberg
(74) *Attorney, Agent, or Firm* — Knobbe, Martens, Olson & Bear, LLP

(57) ABSTRACT

A new and distinct nectarine tree variety, *Prunus persica* var. *nucipersica,* cv. 'Sunectwentythree' is characterized by early ripening, and large sized fruit with a mildly tart-sweet flavor.

1 Drawing Sheet

Latin name of the genus and species claimed: *Prunus persica* var. *nucipersica.*

Variety denomination: 'SUNECTWENTYTHREE'.

BACKGROUND AND SUMMARY OF THE INVENTION

This invention relates to the discovery and asexual propagation of a new and distinct variety of nectarine, *Prunus persica* var. *nucipersica* cv. 'Sunectwentythree'. The new variety was first originated by hybridization in May 2002 by Terry Bacon as breeder number: 'NE117'. The new variety was first evaluated by Terry A. Bacon near Wasco, Calif. in Kern County.

The new variety 'Sunectwentythree' is characterized by early ripening and large sized fruit with a mildly tart-sweet flavor.

The seed parent is 'Sunectwentyone' (U.S. Plant Pat. No. 18,114), and the pollen parent is not known. The parent varieties were first crossed in February 2000, the date of first sowing being February 2001 and the date of first flowering being February 2002. The new nectarine variety 'SUNECTWENTYTHREE' was first asexually propagated by Terry Bacon near Wasco, Kern County, Calif. in June 2004 by budding.

The new variety 'Sunectwentythree' is distinguished from its seed parent, 'Sunectwentyone' (U.S. Plant Pat. No. 18,114), in that the new variety ripens about seven days later than the seed parent The new variety 'Sunectwentythree' is most similar to Zee Fire (U.S. Plant Pat. No. 13,501) but the new variety "Sunectwentythree' differs from Zee Fire (U.S. Plant Pat. No. 13,501) in that the harvest starts earlier. For example, in the Bakersfield, Calif. area the harvest of the new variety starts 5 days earlier than Zee Fire (U.S. Plant Pat. No. 13,501), on May 13 compared to May 18 for Zee Fire (U.S. Plant Pat. No. 13,501). Additionally, the fruit of the new variety 'Sunectwetythree' is also larger in size than the fruit of Zee Fire (U.S. Plant Pat. No. 13,501), about 68 mm versus 66 mm for 'Zee Fire' (U.S. Plant Pat. No. 13,501).

The new variety 'Sunectwentythree' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new nectarine variety 'Sunectwentythree'.

The illustration shows the upper and lower surface of the leaves, an exterior and sectional view of a fruit divided across its suture plane to show flesh color, pit cavity and the stone. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 10 year old 'SUNECTWENTYTHREE' plants on Nemared (unpatented) rootstock grown in the vicinity of Wasco, Kern County, Calif., and is believed to apply to plants of the variety grown under similar conditions of soil and climate elsewhere. Observations were made in 2013.

TREE

General: (Measurements taken on 10 year old tree unless otherwise noted.).

*Size*.—Large. Normal for most nectarine varieties.
*Spread*.—Normal for most nectarine varieties. Reaches spread of 5 m with normal vase pruning.
*Vigor*.—Strong. Approximately 1.8 to 2 meters of growth in the first growing season.
*Growth*.—Upright to spreading.
*Productivity*.—Productive. Fruit set is usually two or more times the desired amount for marketable size fruit. Thinning is necessary.
*Form*.—Vase formed.
*Bearer*.—Regular.
*Fertility*.—Self-fertile.
*Canopy density*.—Dense. Pruning is necessary to maintain tree vase shape and allow light into canopy.
*Hardiness*.—Hardy in all fruit growing areas of California. Chilling requirement is about 400 hours.
*Disease resistance/susceptibility*.—No specific testing for relative plant disease resistance/susceptibility has been undertaken. Under close observation in Kern County, Calif., no particular plant/fruit disease resistance/susceptibility has been observed.
*Type of bearing*.—On long shoots only.
*Position of vegetative bud in relation to one year old shoot*.—Slightly held out/.

Trunk: (Measurements at approximately 30 cm above soil line.).
*Diameter*.—Approximately 25 cm.
*Texture*.—Medium shaggy.
*Trunk color*.—Outer bark is about Light Greyed-Green 198D to 178A Dark Greyed-Red. Trunk color becomes darker with age.

Branches: (Measurements at approximately 90 cm above soil line.).
*Size*.—Diameter ranges from approximately 8-10 cm.
*Texture*.—Smooth on young wood, increasing roughness with tree age.
*Color*.—About Dark Greyed-Orange 166A to Light Greyed-Green 198D.
*Lenticels*.—Present.
*Lenticels numbers*.—Numerous.
*Lenticels density*.—Approximately 3-5 per $cm^2$.
*Lenticels color*.—About Medium Greyed-Orange 164C.
*Lenticels size*.—Medium.
*Lenticels length*.—Approximately 6 mm.
*Lenticels width*.—Approximately 2 mm.

Flowering shoots: (Data taken in June at midpoint of current-season growth.).
*Size*.—Average diameter approximately 5 mm.
*Color*.—Topside: About Dark Greyed-Brown 199A to Dark Green 141B. Underside: About Dark Green 141B.
*Thickness*.—Medium.
*Internode length*.—Medium.
*Flowering shoot lenticels*.—None observed.
*Flowering shoot leaf buds*.—Shape: Obovate. Width: Approximately 2 mm. Length: Approximately 3 mm. Color: About Dark Greyed-Orange 165A.
*Flowering shoot flower buds*.—Shape: Obovate. Width: Approximately 2.5 mm. Length: Approximately 4 mm. Color: About Dark Greyed-Orange 165A. Number of buds per node: Usually 2.
*Presence of anthocyanin coloration*.—Present.
*Density of buds*.—Medium.
*Length on internodes*.—Medium, usually 1 cm midway in the flowering shoots.
*Flower bud distribution*.—Generally isolated on one year old shoots.
*Ratio of wood (leaf) buds to flowering shoots*.—½.

FOLIAGE

Leaves: (Data taken in June on fully expanded leaves).
*Average length*.—Medium; approximately 150 mm.
*Average width*.—Medium; approximately 40 mm.
*Thickness*.—Medium.
*Color*.—About Dark Green 135A.
*Form*.—Lanceolate.
*Tip*.—Acuminate.
*Base*.—V-shaped.
*Margin*.—Crenate.
*Venation*.—Pinately net veined.
*Vein color*.—About Medium Green 138B.
*Red mid vein on lower side*.—Absent.
*Surface texture*.—Smooth.
*Leaf blade (Ratio of length to width)*.—High; approximately 3.75:1 ratio.
*Shape in the cross section*.—Concave.
*Angle at apex*.—Small.
*Angle at base*.—Acute.
*Profile*.—Up folded.
*Leaf blade tip*.—Curved downwardly.
*Angle of tip*.—Acute.
*Undulation of margin*.—Slight.
*Timing of beginning of leaf bud burst*.—Early.

Petiole:
*Average length*.—Medium; approximately 6 mm.
*Average diameter*.—Approximately 0.7 mm.
*Color*.—About Dark Greyed-Red 180A when dry.
*Nectaries*.—Present.
*Shape of nectaries*.—Round.
*Thickness*.—Medium, approximately 1 mm.

Stipules:
*Number/leaf bud*.—Approximately 2 when present.
*Typical length*.—Medium, approximately 8 mm.
*Color*.—About Medium Yellow-Green 151A.
*Persistence*.—Falls off.

Leaf glands:
*Form*.—Globose.
*Average number*.—Usually 2.
*Position*.—On petiole, alternate.
*Average size*.—Medium; approximately 1 mm long.
*Color*.—About Dark Greyed-Red 180A when dry.

FLOWERS

General:
*Flower blooming period*.—First, bloom: Approximately February 14. Location of First bloom: Toward base of tree. Full bloom: Approximately February 18. Location of Full bloom: Midway on tree.
*Time of bloom*.—Medium.
*Duration of bloom*.—Medium; approximately 10 days.
*Type*.—Rosette (showy).
*Time of beginning of flowering*.—Medium.
*Diameter of fully opened flower*.—Medium, approximately 35 mm.
*Flower aroma*.—Very slight.
*Corolla (main color on inner side)*.—About Medium Red-Purple 62C.
*Spurs*.—Absent.

Peduncle:
*Length*.—Medium; approximately 3-4 mm.
*Diameter*.—Medium; approximately 2 mm.
*Color*.—About Medium Yellow-green 146B.
*Pubescence*.—Absent.
Petals:
*Number*.—5.
*Arrangement*.—Slightly overlapping.
*Length*.—Approximately 18 mm.
*Diameter*.—Approximately 15 mm.
*Shape*.—Circular.
*Width* (*rosette flowers only*).—Broad.
*Apex shape*.—Rounded.
*Base shape*.—Narrows at point of attachment.
*Color* (*inner and outer surfaces*).—About Medium Red-Purple 62C.
*Surface texture*.—Smooth.
*Margins*.—Smooth, undulating.
*Frequency of flowers with double petals*.—None.
*Claw length*.—Medium.
*Margin waviness*.—Medium.
*Base angle*.—Narrow.
*Division of upper margin*.—Entire.
*Pubescence of inner surface*.—Absent.
*Pubescence of outer surface*.—Absent.
Sepals:
*Number*.—5.
*Length*.—Approximately 7 mm.
*Diameter*.—Approximately 5 mm.
*Shape*.—Ovate.
*Color*.—About Medium Red 44A.
*Surface texture*.—Smooth to slightly bumpy.
*Margins*.—Smooth.
*Positioning*.—Adpressed to petals.
*Pubescence of inner surface*.—Few.
*Pubescence of outer surface*.—Medium.
*Frequency of flowers with double sepals*.—None.
Stamens:
*Number*.—Approximately 37.
*Average length*.—Approximately 8 mm.
*Filament color*.—White.
*Anther color*.—About Medium Red 52A when drying.
*Flower pollen color*.—About Medium Red 52A.
*Position compared to petals*.—Slightly below.
Pistil:
*Number*.—One, occasionally up to 3.
*Average length*.—Approximately 37 mm.
*Ovary diameter*.—Approximately 1-1.5 mm.
*Pubescence*.—None.
*Stigma extension in comparison to anthers*.—Above.
*Frequency of supplementary pistils*.—Few.
Flower buds:
*Hardiness*.—Hardy.
*Size*.—Medium, approximately 4 mm long and 2.5 mm wide.
*Length*.—Medium.
*Shape*.—Obovate.
*Positioning*.—Free.
*Pubescence*.—Few.
*Color*.—About Dark Greyed-Orange 165A.
Receptacle:
*Depth*.—Medium, approximately 2 mm.
*Pubescence of inner surface*.—Absent.
*Pubescence of outer surface*.—Absent.
Stigma:
*Position* (*as compared to anther*).—Above.
Ovary:
*Pubescence*.—Absent.
Style:
*Pubescence* (*of base*).—Absent.

FRUIT

General: (At firm-ripe, on tree managed to obtain maximum size for commercial production near Wasco, Kern County, Calif. Description taken near Wasco, Kern County, Calif. on May 17, 2013).).
*Harvest*.—
*Date of first pick*.—Approximately May 13.
*Date of last pick*.—Approximately May 23.
Lentils: Absent.
Maturity when described: Firm.
Season ripening: Early.
Position of maximum diameter: Towards the middle.
Symmetry about the suture: Symmetric.
Size:
*Average size*.—Large.
*Length* (*stem end to apex*).—Approximately 72 mm.
*Diameter in line with suture plane*.—Approximately 70 mm.
*Diameter perpendicular to suture plane*.—Approximately 72 mm.
*Average weight*.—Approximately 168 gm.
Shape: Circular.
Apex shape: Rounded.
Apex base: Rounded.
Mucron tip at pistil end: Absent.
Shape of pistil end (excluding mucron tip): Weakly depressed under conditions in Bakersfield, Calif.
Symmetry (viewed from pistil end): Symmetric.
Fruit stem cavity:
*Shape*.—Rounded.
*Depth*.—Medium, approximately 3 mm.
*Breath*.—Approximately 1 cm.
Fruit stem:
*Length*.—Medium, glabrous.
*Diameter*.—Approximately 2 mm.
*Color*.—About Medium Greyed-Orange 164B.
*Adherence to stone*.—Strong.
Fruit skin:
*Thickness*.—Medium, approximately 0.8 mm.
*Adherence to flesh*.—Strong.
*Surface texture*.—Smooth.
*Pubescence*.—Absent.
*Bloom*.—None.
*Ground color*.—About Medium Yellow 11A.
*Overcolor*.—About Dark Red 44B to Dark Red 46A.
*Taste*.—None.
*Firmness*.—Firm.
*Reticulation*.—Absent.
*Roughness*.—Absent.
*Tenacity*.—Tenacious to flesh.
*Relative area of over color of skin*.—Very large.
*Pattern of over color of skin*.—Solid.
*Tendency to crack*.—Slight, in wet season.
Flesh:
*Ripens*.—Evenly.
*Texture*.—Firm-melting flesh.
*Fibers*.—Moderate.

*Flavor*.—Mildly tart-sweet.
*Brix*.—Approximately 12°.
*Juice*.—Moderate.
*Aroma*.—Slight.
*Color*.—About Light Yellow-Orange 21D.
*Sweetness*.—Medium.
*Anthocyanin color of flesh in central part of flesh*.—Absent or very weak.
*Anthocyanin color of flesh next to skin*.—Absent or very weak.
*Anthocyanin color of flesh around stone*.—Absent or very weak.
*Amygdalin*.—Wanting.
*Titratable acidity*.—Approximately 0.8%.
*Eating quality*.—Good.
*Stone/flesh ratio*.—About 1/28 by weight.
*Firmness*.—Firm.

Pit cavity size:
*Length*.—Approximately 35 mm.
*Diameter in line with suture plane*.—Approximately 26 mm.
*Diameter perpendicular to suture plane*.—Approximately 21 mm.
*Color*.—About Medium Yellow 11B.

Depth of stalk cavity: Medium, approximately 3 mm.
Width of stalk cavity: Medium, approximately 1 cm.
Fruit use: Fresh market.
Fruit shipping and keeping quality: Good.
Time of maturity of consumption: Early.

Stone:
*Stone freeness*.—Clings over entire surface.
*Adherence to flesh*.—Present.
*Degree of adherence to flesh*.—Strong.
*Stone size*.—Size: Medium. Size compared to Fruit: Small. Length: Medium, approximately 35 mm. Diameter in line with suture plan): Approximately 26 mm. Diameter perpendicular to suture plane: Approximately 21 mm. Width of Stalk End: Medium; approximately 5 mm. Angle of Stalk end: Right angle. Hilum: Oval.
*Stone form*.—Viewed from stem end: Oval-flattened. Viewed from side: Oval, pointed at apex. Viewed from ventral side: Oval-flattened.
*Stone shape*.—Lateral view: Oval. Base shape: Nearly straight. Apex shape: Pointed.
*Relief of surface*.—Predominately pits.
*Stone surface*.—Pitted throughout.
*Stone halves*.—Nearly symmetric.
*Stone ridges*.—Continuous.
*Stone outgrowing keel*.—Well developed.
*Stone tendency to split*.—Low.
*Anthocyanin coloration*.—Absent.
*Intensity of brown color*.—Light.
*Color*.—About Light Greyed-Orange 164C.
*Position of maximum*.—Middle.
*Sides*.—Equal.
*Pits*.—Circular-to-elongated.
*Fibers*.—Retains short fibre-like threads along ridges.
*Ventrical edge*.—Medium.
*Dorsal edge*.—Full, deep grooves.

Resistance to insects: Unknown.
Resistance to disease: Unknown.

What is claimed is:

1. A new and distinct nectarine tree as herein described and illustrated.

* * * * *

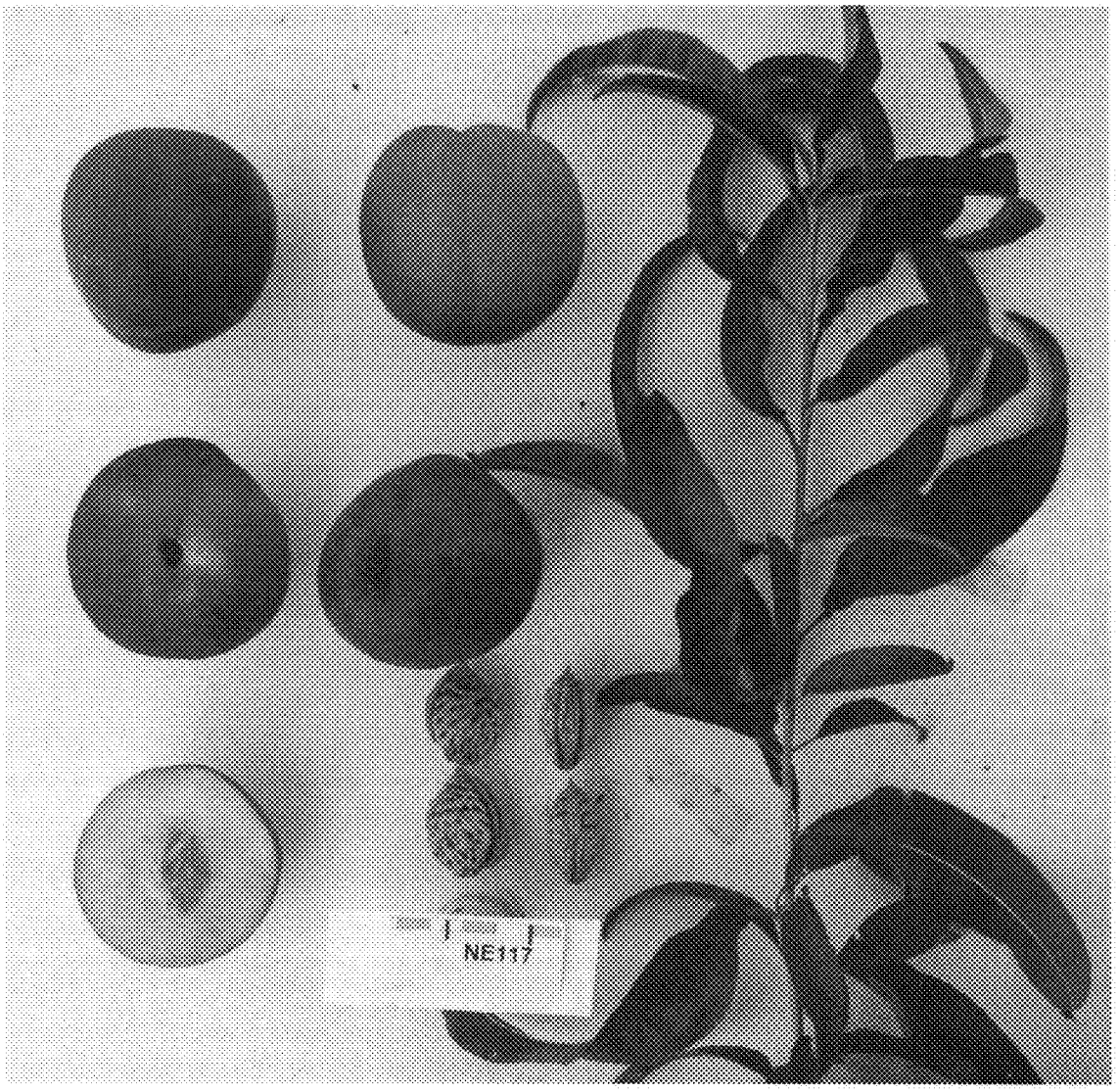
NE117